US006384302B1

(12) United States Patent
Chen et al.

(10) Patent No.: US 6,384,302 B1
(45) Date of Patent: *May 7, 2002

(54) TRYPSIN INHIBITORS WITH INSECTICIDAL PROPERTIES OBTAINED FROM *PENTACLETHRA MACROLOBA*

(75) Inventors: Ruzhu Chen; Karel R. Schubert, both of Norman, OK (US); Thomas H. Czapla, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/321,399

(22) Filed: May 28, 1999

Related U.S. Application Data (63) Continuation of application No. 08/938,975, filed on Sep. 26, 1997, now Pat. No. 5,981,722, which is a continuation-in-part of application No. 08/560,727, filed on Nov. 20, 1995, now Pat. No. 5,672,680.

(51) Int. Cl.$^7$ .............................. A01H 5/00; A01H 5/10; C12N 15/29; C12N 15/82
(52) U.S. Cl. .................... 800/302; 800/279; 800/320.1; 435/418; 435/468
(58) Field of Search ................................. 800/278, 279, 800/298, 301, 302, 320.1; 435/69.1, 320.1, 410, 419, 418, 468; 536/23.6, 23.1

(56) References Cited

U.S. PATENT DOCUMENTS 5,672,680 A  *  9/1997  Chen et al. .................. 530/300
5,981,722 A  *  11/1999  Chen et al. ................. 536/23.1

OTHER PUBLICATIONS

Lazar, E. et al., "Transforming Growth Factor a: Mutation of Aspartic Acid 47 and Leucine 48 Results in Different Biological Activities." 1988, Molecular and Cellular Biology, vol. 8, pp. 1247–1252.*

Hill, M. A. and Preiss, J., "Functional Analysis of Conserved Histidines in ADP–Glucose Pyrophosphorylase from *Escherichia coli*." 1998, Biochemical and Biophysical Research Communications, vol. 244, pp. 573–577.*

Yamamoto et al. (1983) "Amino Acid Sequences of Two Trypsin Inhibitors from Winged Bean Seeds (*Psophocarpus tetragonolobus* (L) DC.)" *J. Biochem* 94:849–863.

Kim et al. (1985) "Comparative Study of Amino Acid Sequences of Kunitz–Type Soybean Trypsin Inhibitors, Ti$^a$, Ti$^b$, and Ti$^c$" *J. Biochem* 98:435–448.

Richardson et al. (1986) "The Amino Acid Sequence and Reactive (Inhibitory) Site of the Major Trypsin Isoinhibitor (DE5) Isolated from Seeds of the Brazilian Carolina Tree (*Adenanthera pavonina* L.)" *Biochimica et Biophysica Acta* 878:134–140.

Ryan, Clarence A. (1990) "Protease Inhibitors in Plants: Genes for Improving Defenses Against Insects and Pathogens" *Annu. Rev. Phytopathol.* 28:425–449.

Negreiros et al. (1991) "The Complete Amino Acid Sequence of the Major Kunitz Trypsin Inhibitor from the Seeds of *Prosopsis Juliflora*" *Phytochemistry* vol. 30, No. 9:2829–2833.

Kingsley, Mbajunwa Obinna (1995) "Effect of Processing on Some Antinutritional Toxic Components and on the Nutritional Composition of the African Oil Bean Seed (*Pentaclethra macrophylla* Benth)" *J. Sci Food Agric* 68:153–158.

Chun et al. (1994) "*Pentaclethra macrobola* Seed Effect on Larval Growth, Cell Viability, and Midgut Enzyme Activity of *Helicoverpa zea* (Lepidoptera: Noctuidae)" *Journal of Economic Entomology* vol. 87, No. 6:1754–1760.

Wu et al. (1993) "The Complete Amino Acid Sequence of a Kunitz Family Trypsin Inhibitor from Seeds of *Acacia Confusa*" *J. Biochem.* 113:258–263.

Napoli et al. (1989) *The Plant Cell* 2:278–289.
Hidler et al. (1989) *Plant Molecular Biology* 13:701–710.
Gordon–Kamm et al. (1990) *Plant Cell* 2:603–618.
Hoffmann et al. (1992) *J. Econ Entomology* 85:2516–2522.

* cited by examiner

Primary Examiner—David T. Fox
Assistant Examiner—Anne Kubelik
(74) Attorney, Agent, or Firm—Alston & Bird LLP (57) ABSTRACT

Compositions and methods for controlling pests, particularly insect pests, are provided. The compositions comprise proteins isolated from plants of the genus Pentaclethra which exhibit trypsin inhibiting activity. Nucleotide sequences encoding the proteins are also provided. Such sequences find use in transforming organisms for control of pests.

6 Claims, 3 Drawing Sheets

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
        (A) LENGTH: 558 base pairs
        (B) TYPE: nucleic acid
        (C) STRANDEDNESS: single
        (D) TOPOLOGY: linear     (ii) MOLECULE TYPE: cDNA     (vi) ORIGINAL SOURCE:
        (A) ORGANISM: PENTACLETHRA MACROLOBA     (ix) FEATURE:
        (A) NAME/KEY: CDS
        (B) LOCATION: 25..387

(xi) SEQUENCE DESCRIPTION: SEQ ID NO: 1:

```
GGCACGAGGA GAGAGAGACA GAAG ATG GGT TTG AAG AAG GCG ACC ATG GTG        51
                          Met Gly Leu Lys Lys Ala Thr Met Val
                           1               5

AAG GTA GGT GTA GTG CTG TTC CTG ATG GCC CTC ACT GCA ACT GTG GAG       99
Lys Val Gly Val Val Leu Phe Leu Met Ala Leu Thr Ala Thr Val Glu
 10              15                  20                  25

GGC CGC TTC GAT TCG AAC ACG TTA CTT GCT CAG GTG ATG ATG AAG GAG      147
Gly Arg Phe Asp Ser Asn Thr Leu Leu Ala Gln Val Met Met Lys Glu
                 30                  35                  40

AAT GGT GAA CCC AAC TAC TTC ATC AAG TCC ACC ACC ACC GCC TGC TGC      195
Asn Gly Glu Pro Asn Tyr Phe Ile Lys Ser Thr Thr Thr Ala Cys Cys
             45                  50                  55

GAC AAC TGC CCT TGC ACA AAG TCA AAC CCA CCT CAA TGC CAA TGC AAT      243
Asp Asn Cys Pro Cys Thr Lys Ser Asn Pro Pro Gln Cys Gln Cys Asn
         60                  65                  70

GAT TGG AAA GAA ACT TGC CAC TCC GCT TGT AAG ACC TGT ATT TGC AGG      291
Asp Trp Lys Glu Thr Cys His Ser Ala Cys Lys Thr Cys Ile Cys Arg
```

```
                75                     80                     85
GCA ATA TAT CCT CCA CAG TGT CGT TGT TTT GAT ACC AAC AAC TTC TGC         339
Ala Ile Tyr Pro Pro Gln Cys Arg Cys Phe Asp Thr Asn Asn Phe Cys
 90              95                     100                105

TAT CCT CCT TGC CCC TCT TCT GCT GCC AAA CCT CAA CTT GCG AAC TGA         387
Tyr Pro Pro Cys Pro Ser Ser Ala Ala Lys Pro Gln Leu Ala Asn  *
                110                    115                    120

TCGTCGTTAA TGGTGTGATG TTATGTGAAC GAAGCCCTCT ACTGCTCTAG GCTTTGTTTC       447

TATATATGTA CGTGAATGTG AAGCATATCT AATAAAATAA GATATCGTGG GCCTTTCTTC       507

CAGTTTGCTT TTTGCAAACT GGCTGCTTGC AGGCTCTTGA TCTTCTTCAA A                558
```

(2) INFORMATION FOR SEQ ID NO: 2:

(i) SEQUENCE CHARACTERISTICS:
        (A) LENGTH: 120 amino acids
        (B) TYPE: amino acid
        (D) TOPOLOGY: linear     (ii) MOLECULE TYPE: protein     (xi) SEQUENCE DESCRIPTION: SEQ ID NO: 2:

```
Met Gly Leu Lys Lys Ala Thr Met Val Lys Val Gly Val Val Leu Phe
 1               5                      10                     15

Leu Met Ala Leu Thr Ala Thr Val Glu Gly Arg Phe Asp Ser Asn Thr
                20                     25                     30

Leu Leu Ala Gln Val Met Met Lys Glu Asn Gly Glu Pro Asn Tyr Phe
                35                     40                     45

Ile Lys Ser Thr Thr Thr Ala Cys Cys Asp Asn Cys Pro Cys Thr Lys
                50                     55                     60

Ser Asn Pro Pro Gln Cys Gln Cys Asn Asp Trp Lys Glu Thr Cys His
 65                     70                     75                     80

Ser Ala Cys Lys Thr Cys Ile Cys Arg Ala Ile Tyr Pro Pro Gln Cys
                85                     90                     95

Arg Cys Phe Asp Thr Asn Asn Phe Cys Tyr Pro Pro Cys Pro Ser Ser
                100                    105                    110

Ala Ala Lys Pro Gln Leu Ala Asn
                115                    120
```

(2) INFORMATION FOR SEQ ID NO: 3:

(i) SEQUENCE CHARACTERISTICS:
        (A) LENGTH: 35 amino acids
        (B) TYPE: amino acid
        (C) STRANDEDNESS: single
        (D) TOPOLOGY: linear     (ii) MOLECULE TYPE: peptide     (v) FRAGMENT TYPE: N-terminal     (vi) ORIGINAL SOURCE:
        (A) ORGANISM: Pentaclethra macroloba     (xi) SEQUENCE DESCRIPTION: SEQ ID NO: 3:

```
Glu Val Val Phe Asp Phe Lys Gly Asp Met Met Arg Asn Gly Gly His
 1               5                      10                     15

Tyr Tyr Phe Phe Pro Ala Ala Pro Tyr Gly Gly Gly Asn Leu Leu Ala
                20                     25                     30

Ala Ala Val
                35
```

TRYPSIN INHIBITORS WITH INSECTICIDAL PROPERTIES OBTAINED FROM *PENTACLETHRA MACROLOBA*

RELATED INVENTION

This application is a Continuation of application Ser. No. 08/938,975, filed Sep. 26, 1997, now U.S. Pat. No. 5,981,722, and entitled TRYPSIN INHIBITORS WITH INSECTICIDAL PROPERTIES OBTRAINED FROM *PENTACLETHRA MACROLOBA*, which is hereby incorporated herein in its entirety, which is a Continuation-In-Part of Ser. No. 08/560,727, filed Nov. 20, 1995 now U.S. Pat. No. 5,672,680, and entitled *PENTACLETHRA MACROLOBA* PROTEIN HAVING INSECTICIDAL PROPERTIES. The specification of the copending application is incorporated herein by reference. This application and the copending application are owned by a common assignee.

FIELD OF THE INVENTION

The invention relates to methods and materials for controlling insect species. In particular, the invention relates to insecticidal proteins, DNA sequences encoding such proteins, and the genetic manipulation of plants and other organisms.

BACKGROUND OF THE INVENTION

Numerous insect species are serious pests to common agricultural crops such as corn, soybeans, peas and similar crops. During the last century, the primary method of controlling such pests has been through the application of synthetic chemical insecticidal compounds. However, as the use of such chemical compounds proliferated and continued, it became evident that such wide-spread use posed problems with regard to the non-selectivity of the compounds, the increasing insect resistance to the chemicals and the environmental affect of such compounds, after run-off, on higher order species such as fish and birds among others. As a result of such problems, other methods of controlling insect pests were sought and tried.

One such alternative method of pest control has been the use of biological organisms which are typically "natural predators" of the species sought to be controlled. Such predators may include other insects, fungi (milky-spore) and bacteria such as *Bacillus thuringiensis* cv. Alternatively, large colonies of an insect pest have been captively raised, sterilized and released into the environment in the hope that mating between the sterilized insects and fecund wild insects will decrease the insect population. While both these approaches have had some success, they entail considerable expense and present several major difficulties. For example, it is difficult both to apply living biological organisms to large areas and to cause such organisms to remain in the treated area or on the treated plant species for an extended time. Predator insects can migrate and fungi or bacteria can be washed off a plant or removed from a treated area by rain. Consequently, while the use of such biological controls has desirable characteristics and has met with some success, in practice these methods seem severely limited. However, scientific advances seem to offer new opportunities for controlling insect pests.

Advances in biotechnology in the last two decades have presented new opportunities for pest control through genetic engineering. In particular, advances in plant genetics coupled with the identification of insect growth factors and naturally-occurring plant defensive compounds or agents offer the opportunity to create transgenic crop plants capable of producing such defensive agents and thereby protect the plants against insect attack.

Scientists have identified some specific plant components or compounds which act as defensive agents to protect a plant from attack by insect pests and pathogens. While such components are usually present at only low levels in various plant tissues, some of them are also capable of being induced to higher levels upon attack by an insect pest or a pathogen. Examples of such defensive compounds include alkaloids, terpenes, and various proteins such as enzymes, enzyme inhibitors, and lectins.

Of particular interest are enzyme inhibitors that can block enzymatic activity and inhibit insect growth. For example, trypsin is a digestive enzyme. Its role in a body is to hydrolyze polypeptides into smaller units which can then be utilized by the host subject, for example, an insect. Blocking trypsin activity will inhibit insect growth. A trypsin inhibitor (abbreviated TI) is thus a compound which will block or decrease trypsin protease activity. As a result of such blockage or decrease in trypsin protease activity, a host subject which has ingested TI with its food will obtain little or no benefit from the polypeptides contained in the food. The host may thus fail to grow, mature and may indeed ultimately starve and die.

Trypsin inhibitors and lectins have been reported in the seeds of a number of leguminous tropical plants. The proposed role of such trypsin inhibitors (TIs) in plant defense has been shown using transgenic plants expressing a TI gene. Hilder et al. (1987) *Nature* 330:160–163, introduced the Bowman-Birk TI gene from soybeans into tobacco plants and showed that the transgenic plants were able to resist damage from a lepidopteran insect. Transformation and expression of other TI genes such as potato TI I and II also resulted in transgenic plants which showed resistance to insect attack. In the same experiments, transgenic plants which contained an unexpressed TI gene were susceptible to insect attack (See, Johnson et al. (1989) *Proc. Natl. Acad. Sci. USA* 86:9871–9875).

Transgenic plants that are resistant to specific insect pests have been produced using genes encoding *Bacillus thuringiensis* (Bt) endotoxins or plant protease inhibitors (PIs). Transgenic plants containing Bt endotoxin genes have been shown to be effective for control of some insects. Effective plant protection using transgenically inserted PI genetic material has not yet been demonstrated in the field. While cultivars expressing Bt genes may presently exhibit resistance to some insect pests, resistance based on the expression of a single gene might eventually be lost due to the evolution of Bt resistance in the insects. Thus, the search for additional genes that can be inserted into plants to provide protection from insect pests are needed.

SUMMARY OF THE INVENTION

Compositions and methods for the control of insects and other pests are provided. The compositions comprise proteins having pesticidal activities which can be isolated from leguminous plants. Particularly, the invention identifies and provides trypsin inhibitors obtainable from the genus, Pentaclethra, said inhibitors being approximately 38–45 and approximately 6–9 kilodaltons (kDa) in size. Purified protein, as well as amino acid and DNA sequence information is provided for proteins having insecticidal activity. The DNA sequences encoding the pesticidal proteins can be used to transform plants, bacteria, and other organisms for the control of pests.

The compositions and methods of the invention may be used in a variety of systems for controlling plant and non-plant pests.

DETAILED DESCRIPTION OF THE INVENTION

Compositions and methods for controlling pests, particularly plant pests, are provided. In particular, novel pesticidal proteins are provided. The proteins are purified from members of the family Leguminosae, particularly the Leguminous genus Pentaclethra, more particularly the species P. macrophylla and P. macroloba.

In accordance with the invention, the pesticidal proteins produced by members of the genus Pentaclethra can be isolated by methods known in the art. In particular, the proteins of the invention have insecticidal activity. By insecticidal is intended that the proteins of the invention inhibit insect growth generally leading to death of the insect. The proteins of the invention exhibit trypsin inhibiting activity. Thus, after ingestion of the proteins by an insect, the insect fails to grow and often dies.

Proteins of interest are trypsin inhibitors. Such proteins can be used for pest control in plants, particularly by transforming a plant of interest with the trypsin inhibitor. Trypsin inhibitors (TIs) from different plant species have considerably different inhibitive constants ($K_i$ values). See, for example, Belitz et al. (1982) Z. Lebensm. Unters.-Forsch 174:442–446 and Christeller et al. (1989) Insect Biochem. 19:233–241. The TIs of the invention may be screened to determine that the proteins when expressed in a transgenic crop plant will have sufficient resistance to insect attack. Such methods of testing the insecticidal activity of proteins are available in the art. See, in particular, the assays described in the Experimental Section.

The insecticidal proteins of the invention may be classified into at least two classes based upon size of the protein and range of insects killed upon ingestion of the protein. These two classes include proteins in the range of about 6 to about 9 kDa designated PmSTI and proteins in the range of about 38 to about 45 kDa designated PmLTI. Proteins from such classes can be tested for insecticidal activity against a range of insects by bioassay techniques known in the art.

The highest concentration of the trypsin inhibitors of the invention occurs in plant storage organs such as seeds and tubers. Such tissues are a source of additional trypsin inhibitors.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

Methods for protein isolation include conventional chromatography, including gel-filtration, ion-exchange, and affinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. See for example Current Protocols in Molecular Biology, Vols. 1 and 2, Ausubel et al. (eds.), John Wiley & Sons, NY (1988), herein incorporated by reference.

Once purified protein is isolated, the protein, or the polypeptides of which it is comprised, can be characterized and sequenced by standard methods known in the art. For example, the purified protein, or the polypeptides of which it is comprised, may be fragmented as with cyanogen bromide, or with proteases such as papain, chymotrypsin, trypsin, lysyl-C endopeptidase, etc. (Oike et al. (1982) J. Biol. Chem. 257:9751–9758; Liu et al. (1983) Int. J. Pept. Protein Res. 21:209–215). The resulting peptides are separated, preferably by HPLC, or by resolution of gels and electroblotting onto PVDF membranes, and subjected to amino acid sequencing. To accomplish this task, the peptides are preferably analyzed by automated sequenators. It is recognized that N-terminal, C-terminal, or internal amino acid sequences can be determined. From the amino acid sequence of the purified protein, a nucleotide sequence can be synthesized which can be used as a probe to aid in the isolation of the gene encoding the pesticidal protein.

In the same manner, antibodies raised against partially purified or purified peptides can be used to determine the spatial and temporal distribution of the protein of interest. Thus, the tissue where the protein is most abundant, and possibly more highly expressed can be determined and expression libraries constructed. Methods for antibody production are known in the art. See, for example Antibodies, A Laboratory Manual, Harlow and Lane (eds), Cold Spring Harbor Laboratory Press, Cold Spring Harbor, N.Y. (1988), and the references cited therein. See also, Radka et al. (1983) *J. Immunol.* 128:2804; and Radka et al. (1984) *Immunogenetics* 19:63. Such antibodies can be used to isolate proteins with similar binding domains and the proteins tested for activity against insect pests of interest.

It is recognized that any combination of methods may be utilized to purify proteins having pesticidal properties. As an isolation protocol is being determined, the pesticidal activity can be tested for each fraction of material obtained after each purification step.

Such purification protocols will result in a substantially purified protein fraction. By "substantially purified" or "substantially pure" is intended protein which is substantially free of any compound normally associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase or capillary electrophoresis. The terms "substantially pure" or "substantially purified" are not meant to exclude artificial or synthetic mixtures of the proteins with other compounds. The terms are also not meant to exclude the presence of minor impurities which do not interfere with the biological activity of the protein, and which may be present, for example, due to incomplete purification.

From fragments of the protein, the entire nucleotide sequence encoding the protein can be determined by PCR experiments. Likewise, fragments obtained from PCR experiments can be used to isolate cDNA sequences from expression libraries. See, for example, Molecular Cloning, A Laboratory Manual, Second Edition, Vols. 1–3, Sambrook et al. (eds.) Cold Spring Harbor Laboratory Press, Cold Spring Harbor, N.Y. (1989), and the references cited therein.

In this manner, proteins and the nucleotide sequences encoding such proteins can be isolated which are inhibitory or toxic to particular insect species. In particular, proteins and nucleotide sequences which are inhibitory or toxic to insects of the orders Lepidoptera and Coleoptera can be obtained. Such proteins and nucleotide sequences of the invention can be utilized to protect plants from pests, including insects, fungi, bacteria, nematodes, viruses or viroids, and the like, particularly insect pests. Nematodes include parasitic nematodes such as root knot, cyst and lesion nematodes.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* surgarcane borer; *Diabrotica virgifera,* western corn rootworm; *Diabrotica longicornis barberi,* northern corn rootworm; *Diabrotica undecimpunctata howardi,* southern corn rootworm; Melanotus spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn flea beetle; *Sphenophorus maidis,* maize billbug; *Rhopalosiphum maidis,* corn leaf aphid; *Anuraphis maidiradicis,* corn root aphid; *Blissus leucopterus leucopterus,* chinch bug; *Melanoplus femurrubrum,* redlegged grasshopper; *Melanoplus sanguinipes,* migratory grasshopper; *Hylemya platura,* seedcorn maggot; *Agromyza parvicornis,* corn blot leafminer; *Anaphothrips obscrurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; Eleodes, Conoderus, and Aeolus spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; *Blissus leucopterus leucopterus,* chinch bug; *Contarinia sorghicola,* sorghum midge; *Tetranychus cinnabarinus,* carmine spider mite; *Tetranychus urticae,* twospotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia,* western cutworm; *Elasmopalpus lignosellus,* lesser cornstalk borer; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarctata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; zygogramma exclamationis, sunflower beetle; *Bothyrus gibbosus,* carrot beetle; *Neolasioptera murtfeldtiana,* sunflower seed midge; Cotton: *Heliothis virescens,* cotton budworm; *Helicoverpa zea,* cotton bollworm; *Spodoptera exigua,* beet armyworm; *Pectinophora gossypiella,* pink bollworm; *Anthonomus grandis,* boll weevil; *Aphis gossypii,* cotton aphid; *Pseudatomoscelis seriatus,* cotton fleahopper; *Trialeurodes abutilonea,* bandedwinged whitefly; *Lygus lineolaris,* tarnished plant bug; *Melanoplus femurrubrum,* redlegged grasshopper; *Melanoplus differentialis,* differential grasshopper; *Thrips tabaci,* onion thrips; *Franklinkiella fusca,* tobacco thrips; *Tetranychus cinnabarinus,* carmine spider mite; *Tetranychus urticae,* twospotted spider mite; Rice: *Diatraea saccharalis,* sugarcane borer; *Spodoptera frugiperda,* fall armyworm; *Helicoverpa zea,* corn earworm; *Colaspis brunnea,* grape colaspis; *Lissorhoptrus oryzophilus,* rice water weevil; *Sitophilus oryzae,* rice weevil; *Nephotettix nigropictus,* rice leafhopper; *Blissus leucopterus* leucopterus, chinch bug; *Acrosternum hilare,* green stink bug; Soybean: *Pseudoplusia includens,* soybean looper; *Anticarsia gemmatalis,* velvetbean caterpillar; *Plathypena scabra,* green cloverworm; *Ostrinia nubilalis,* European corn borer; *Agrotis ipsilon,* black cutworm; *Spodoptera exigua,* beet armyworm; *Heliothis virescens,* cotton budworm; *Helicoverpa zea,* cotton bollworm; *Epilachna varivestis,* Mexican bean beetle; *Myzus persicae,* green peach aphid; *Empoasca fabae,* potato leafhopper; *Acrosternum hilare,* green stink bug; *Melanoplus femurrubrum,* redlegged grasshopper; *Melanoplus differentialis,* differential grasshopper; *Hylemya platura,* seedcorn maggot; *Sericothrips variabilis,* soybean thrips; *Thrips tabaci,* onion thrips; *Tetranychus turkestani,* strawberry spider mite; *Tetranychus urticae,* twospotted spider mite; Barley: *Ostrinia nubilalis,* European corn borer; *Agrotis ipsilon,* black cutworm; *Schizaphis graminum,* greenbug; *Blissus leucopterus leucopterus,* chinch bug; *Acrosternum hilare,* green stink bug; *Euschistus servus,* brown stink bug; *Delia platura,* seedcorn maggot; *Mayetiola destructor,* Hessian fly; Petrobia latens, brown wheat mite; Oil Seed Rape: *Brevicoryne brassicae,* cabbage aphid; *Phyllotreta cruciferae,* Flea beetle; *Mamestra configurata,* Bertha armyworm; *Plutella xylostella,* Diamond-back moth; Delia ssp., Root maggots.

The nucleotide sequences of the invention can be used to isolate other homologous sequences in other plant species, particularly other Leguminous species, more particularly other Pentaclethra species. Methods are readily available in the art for the hybridization of nucleic acid sequences. Coding sequences from other plants may be isolated according to well known techniques based on their sequence homology to the coding sequences set forth herein. In these techniques all or part of the known coding sequence is used as a probe which selectively hybridizes to other pesticidal coding sequences present in a population of cloned genomic DNA fragments or cDNA fragments (i.e. genomic or cDNA libraries) from a chosen organism.

For example, the entire trypsin inhibitor sequence or portions thereof may be used as probes capable of specifically hybridizing to corresponding coding sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify the trypsin inhibitor coding sequences of interest from a chosen organism by the well-know process of polymerase chain reaction (PCR). This technique may be used to isolate additional coding sequences from a desired organism or as a diagnostic assay to determine the presence of coding sequences in an organism.

Such techniques include hybridization screening of plated DNA libraries (either plaques or colonies; see, e.g.. Sambrook et al., *Molecular Cloning,* eds., Cold Spring Harbor Laboratory Press (1989)) and amplification by PCR using oligonucleotide primers corresponding to sequence domains conserved among the amino acid sequences (see, e.g. Innis et al., *PCR Protocols, a Guide to Methods and Applications,* eds., Academic Press (1990)).

For example, hybridization of such sequences may be carried out under conditions of reduced stringency, medium stringency or even stringent conditions (e.g., conditions represented by a wash stringency of 35–40% Formamide with 5×Denhardt's solution, 0.5 % SDS and 1×SSPE at 37° C.; conditions represented by a wash stringency of 40–45% Formamide with 5×Denhardt's solution, 0.5% SDS, and 1×SSPE at 42° C.; and conditions represented by awash stringency of 50% Formamide with 5×Denhardt's solution, 0.5% SDS and 1×SSPE at 42° C., respectively), to DNA encoding the insecticidal genes disclosed herein in a standard hybridization assay. See J. Sambrook et al., *Molecular Cloning, A Laboratory Manual 2d* Ed. (1989) Cold Spring Harbor Laboratory. In general, sequences which code for the trypsin inhibitors and other insecticidal proteins of the invention and hybridize to the gene disclosed herein will be at least 50% homologous, 70% homologous, and even 85% homologous or more with the disclosed sequence. That is, the sequence similarity of sequences may range, sharing at least about 50%, about 70%, and even about 85% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif., GAP, BESTFIT, BLAST,, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237–244 (1988); Higgins and Sharp, *CABIOS* 5:151–153 (1989); Corpet, et al., *Nucleic Acids Research* 16:10881–90 (1988); Huang, et al., *Computer Applications in the Biosciences* 8:155–65 (1992), and Person, et al., *Methods of Molecular Biology* 24:307–331 (1994); preferred computer alignment methods also include the BLASTP, BLASTN, and BLASTX algorithms. Altschul, et al., *J. Mol. Biol.* 215:403–410 (1990). Alignment is also often performed by inspection and manual alignment.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. When sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid sequences for these purposes normally means sequence identity of at least 60%, more preferably at least 70%, 80%, 90%, and most preferably at least 95%. Polypeptides which are "substantially similar" share sequences as noted above except that residue positions which are not identical may differ by conservative amino acid changes.

Another indication that nucleotide sequences are substantially identical is if two molecules hybridize to each other under stringent conditions. Generally, stringent conditions are selected to be about 5° C. to about 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent wash conditions are those in which the salt concentration is about 0.02 molar at pH 7 and the temperature is at least about 50, 55, or 60° C. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

It is recognized that the pesticidal proteins may be oligomeric and will vary in molecular weight, number of promoters, component peptides, activity against particular pests, and in other characteristics. However, by the methods set forth herein, proteins active against a variety of pests may be isolated and characterized.

In one embodiment of the invention, trypsin inhibitors obtainable from *Pentaclethra macroloba*, are provided. The trypsin inhibitors are approximately 38–45 and approximately 6–9 kilodaltons (kDa) in size. The 38–45 kDa species, called herein PmLTI, comprises a 43 kDa species having a N-terminal sequence of Glu-Val-Val-Phe-Asp-Phe-Lys-Gly-Asp-Met-Met-Arg-Asn-Gly-Gly-His-Tyr-Tyr-Phe-Phe-Pro-Ala-Ala-Pro-Tyr-Gly-Gly-Gly-Asn-Leu-Leu-Ala-Ala-Ala-Val (shortened nomenclature: EVVFDFKGDMMRNGGHYYFFPAAPYGGGNLLAAAV) (SEQ ID NO: 3).

The 6–9 kDa species, called herein PmSTI, comprises the following amino acid sequence set forth in SEQ ID NO: 2. The cDNA sequence of PmSTI is provided in SEQ ID NO: 1.

The proteins of the invention can be used to protect plants against insect attack, particularly European corn borer, *Helicoverpa zea*, and corn rootworms as well as from nematodes. Such methods are described in more detail below.

The proteins of the invention may be altered in various ways including amino acid substitutions, deletions, truncations, and insertions. Methods for such manipulations are generally known in the art. For example, amino acid sequence variants of the pesticidal proteins can be prepared by mutations in the DNA. Methods for mutagenesis and nucleotide sequence alterations are well known in the art. See, for example, Kunkel, T. (1985) *Proc. Natl. Acad. Sci. USA* 82:488–492; Kunkel et al. (1987) *Methods in Enzymol.* 154:367–382; U.S. Pat. No. 4,873,192; Walker and Gaastra (eds.) *Techniques in Molecular Biology*, MacMillan Publishing Company, NY (1983) and the references cited therein. Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the pesticidal proteins as well as components and fragments thereof. That is, it is recognized that component polypeptides or fragments of the proteins may be produced which retain pesticidal activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by insect toxicity assay.

The proteins or other component polypeptides described herein may be used alone or in combination with other proteins or agents to control different insect pests. Other insecticidal proteins include those from Bacillus, including δ-endotoxins and vegetative insecticidal proteins, as well as protease inhibitors (both serine and cysteine types), lectins, α-amylase inhibitors, peroxidase, and the like.

In one preferred embodiment, expression of the proteins of the invention in a transgenic plant is accompanied by the expression of one or more *Bacillus thuringiensis* (Bt) -endotoxins. This co-expression of more than one insecticidal principle in the same transgenic plant can be achieved by genetically engineering a plant to contain and express such genes. Alternatively, a plant, Parent 1, can be genetically engineered for the expression of at least one of the proteins of the invention. A second plant, Parent 2, can be genetically engineered for the expression of other principles, such as a Bt -endotoxin. By crossing Parent 1 with Parent 2, progeny plants are obtained which express all the genes introduced into Parents 1 and 2.

The present invention also encompasses nucleotide sequences from organisms other than Pentaclethra, where the proteins cross-react with antibodies raised against the proteins of the invention or where the nucleotide sequences are isolatable by hybridization with the nucleotide sequences of the invention. The proteins isolated or those encoded by such nucleotide sequences can be tested for pesticidal activity. The isolated proteins can be assayed for pesticidal activity by the methods disclosed herein or others well-known in the art.

Once the nucleotide sequences encoding the pesticidal proteins of the invention have been isolated, they can be manipulated and used to express the protein in a variety of hosts including microorganisms and plants. It is recognized that the proteins and DNA sequences of the invention may be used alone or in combination with other pesticidal proteins.

The proteins of the invention may be used for protecting agricultural crops and products from pests by introduction via a suitable vector into a microbial host, and said host applied to the environment or plants. Microorganism hosts may be selected which are known to occupy the "phytosphere" (phylloplane, phyllosphere, rhizosphere, and/or rhizoplane) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

The proteins of the invention can be used in expression cassettes for expression in any host of interest. Such expression cassettes will comprise a transcriptional initiation region linked to the gene encoding the pesticidal protein of interest. Such an expression cassette can be provided with a plurality of restriction sites for insertion of the gene of interest to be under the transcriptional regulation of the regulatory regions. The expression cassette may additionally contain selectable marker genes suitable for the particular host organism to be used.

The transcriptional initiation region, or promoter, may be native or endogenous or foreign or heterologous to the host. Additionally, the promoter may be the natural sequence or alternatively a synthetic sequence. By foreign is intended that the transcriptional initiation region is not found in the wild-type host into which the transcriptional initiation region is introduced. As used herein a chimeric gene comprises a coding sequence operably linked to a transcription initiation region which is heterologous to the coding sequence. While any promoter or promoter element capable of driving expression of a coding sequence can be utilized, of particular interest for expression in plants are root promoters (Bevan et al. (1993) in *Gene Conservation and Exploitation. Proceedings of The 20th Stadler Genetics Symposium,* Gustafson et al. (eds.), Plenum Press, New York pp. 109–129; Brears et al. (1991) *Plant J.* 1:235–244; Lorenz et al. (1993) Plant J 4:545–554; U.S. Pat. Nos. 5,459,252; 5,608,149; 5,599,670); pith (U.S. Pat. Nos. 5,466,785; 5,451,514; 5,391,725); or other tissue specific and constitutive promoters (See, for example, U.S. Pat. Nos. 5,608,149; 5,608,144; 5,604,121; 5,569,597; 5,466,785; 5,399,680; 5,268,463; 5,608,142), herein incorporated by reference.

The transcriptional cassette will include in the 5'-3' direction, the orientation of transcription, a transcriptional initiation region, a translational initiation region, a DNA sequence of interest, a translational termination region, and a transcriptional termination region functional in plants. The termination region may be native with respect to the transcriptional initiation region, may be native with respect to the DNA sequence of interest, or may be derived from other sources. Convenient termination regions are available from the Ti-plasmid of *A. tumefaciens,* such as the octopine synthase and nopaline synthase termination regions. See also, Guerineau et al., (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

The sequences of the invention can be targeted to the chloroplast. In this manner, where the gene of interest is not directly inserted into the chloroplast, the expression cassette will additionally contain a gene encoding a transit peptide to direct the gene of interest to the chloroplasts. Such transit peptides are known in the art. See, for example, Von Heijne et aL (1991) *Plant Mol. Biol. Rep.* 9: 104–126; Clark et al. (1989) *J. Biol. Chem.* 264: 17544–17550; Della-Cioppa et al. (1987) *Plant Physiol.* 84: 965–968; Romer et al. (1993) *Biochem. Biophys. Res Commun.* 196: 1414–1421; and, Shah et al. (1986) *Science* 233: 478–481. Plant carotenoid genes useful in the invention may utilize native or heterologous transit peptides.

The nucleotide sequences encoding the proteins or polypeptides of the invention are particularly useful in the genetic manipulation of plants. In this manner, the genes of the invention are placed into expression cassettes for expression in the plant of interest. The cassette will include 5' and 3' regulatory sequences operably linked to the gene of interest. The cassette may additionally contain at least one additional gene to be cotransformed into the organism. Alternatively, other gene(s) of interest can be provided on other expression cassettes. Where appropriate, the gene(s) may be optimized for increased expression in the transformed plant. That is, the genes can be synthesized using plant preferred codons for improved expression. Methods are available in the art for synthesizing plant preferred genes. See, for example, U.S. Pat. Nos. 5,380,831, 5,436, 391, and Murray et al. (1989) *Nucleic Acids Res.* 1 7:477–498, herein incorporated by reference.

Additional sequence modifications are known that enhance gene expression in a cellular host. These include elimination of sequences encoding spurious polyadenylation signals, exon-intron splice site signals, transposon-like repeats, and. other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translational leaders are known in the art and include: picornavirus leaders, for example, EMCV leader (Encephalomyocarditis 5' noncoding region) (Elroy-Stein, O., Fuerst, T. R., and Moss, B. (1989) *PNAS USA,* 86:6126–6130); potyvirus leaders, for example, TEV leader (Tobacco Etch Virus) (Allison et al. (1986); MDMV leader (Maize Dwarf Mosaic Virus); *Virology,* 154:9–20), and human immunoglobulin heavy-chain binding protein (BiP), (Macejak, D. G., and P. Sarnow (1991) *Nature,* 353:90–94; untranslated leader from the coat protein mRNA of alfalfa mosaic virus (AMV RNA 4), (Jobling, S. A., and Gehrke, L., (1987) *Nature,* 325:622–625; tobacco mosaic virus leader (TMV), (Gallie, D. R. et al. (1989) *Molecular Biology of RNA,* pages 237–256; and maize chlorotic mottle virus leader (MCMV) (Lommel, S. A. et al. (1991) *Virology,* 81:382–385). See also, Della-Cioppa et al. (1987) *Plant Physiology,* 84:965–968. Other methods known to enhance expression can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, PCR, or the like may be employed, where insertions, deletions or substitutions, e.g. transitions and transversions, may be involved.

The compositions of the present invention can be used to transform any plant. In this manner, genetically modified plants, plant cells, plant tissue, seed, and the like can be obtained. Transformation protocols may vary depending on the type of plant or plant cell, i.e. monocot or dicot, targeted for transformation. Suitable methods of transforming plant cells include microinjection (Crossway et al. (1986) *Biotechniques* 4:320–334), electroporation (Riggs et al (1986) *Proc. Natl. Acad. Sci. USA,* 83:5602–5606, Agrobacterium mediated transformation (Hinchee et al. (1988) *Biotechnology,* 6:915–921), direct gene transfer (Paszkowski et al. (1984) *EMBO J.,* 3:2717–2722), and ballistic particle acceleration (see, for example, Sanford et al., U.S. Pat. No. 4,945,050; Wo91/10725 and McCabe et al. (1988) *Biotechnology,* 6:923–926). Also see, Weissinger et al. (1988) *Annual Rev. Genet.,* 22:421–477; Sanford et al. (1987) *Particulate Science and Technology,* 5:27–37 (onion); Christou et al. (1988) *Plant Physiol.* 87:671–674 (soybean); McCabe et al. (1988) *Bio/Technology,* 6:923–926 (soybean); Datta et al. (1990) *Biotechnology,* 8:736–740 (rice); Klein et al. (1988) *Proc. Natl. Acad. Sci. USA,* 85:4305–4309(maize); Klein et al. (1988) *Biotechnology,* 6:559–563 (maize); WO91/10725 (maize); Klein et al. (1988) *Plant Physiol.,* 91:440–444(maize); Fromm et al. (1990) *Biotechnology,* 8:833–839; and Gordon-Kamm et al. (1990) *Plant Cell,* 2:603–618 (maize); Hooydaas-Van Slogteren & Hooykaas (1984) *Nature (London),* 311:763–764; Bytebier et al. (1987) *Proc. Natl. Acad. Sci. USA,* 84:5345–5349 (Liliaceae); De Wet et al. (1985) In *The Experimental Manipulation of Ovule Tissues,* ed. G. P. Chapman et al., pp. 197–209. Longman, N.Y. (pollen); Kaeppler et al. (1990) *Plant Cell Reports,* 9:415–418; and Kaeppler et al. (1992) *Theor. Appl. Genet.,* 84:560–566 (whisker-mediated transformation); D=Halluin et al. (1992) *Plant Cell,* 4:1495–1505 (electroporation); Li et al. (1993) *Plant Cell Reports,* 12:250–255 and Christou and Ford (1995) *Annals of Botany,* 75:407–413 (rice); Osjoda et al. (1996) *Nature Biotechnology,* 14:745–750 (maize via *Agrobacterium tumefaciens*); all of which are herein incorporated by reference.

The cells which have been transformed may be grown into plants in accordance with conventional ways. See, for example, McCormick et al. (1986) *Plant Cell Reports,* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The proteins will be expressed in the transformed organisms in amounts to be toxic to the insects of interest or inhibitory to insect growth.

The following examples are offered by way of illustration and not by way of limitation.

Experimental

*P. macroloba* seeds were collected at the La Selva Biological Station, Costa Rica and transported to the inventor's laboratories where they were sliced, lyophilized and stored at −20° C. prior to use. Seed extract was prepared as described by Rathburn et al. (H. Rathbum et al., *J. Econo. Ento.* (submitted)) with and without heating as noted here. Heating was accomplished by boiling sliced seeds in 0.1 M Tris-Cl, pH 8.5, 5 mM $MgCl_2$ before homogenization.

Both trypsin and anhydrotrypsin affinity chromatography, designated TAC and ATAC respectively, were used to isolate trypsin inhibitors from crude extracts. Anhydrotrypsin was prepared according to the method of Pusztal (A. Pustzai et al., *Anal. Biochem.* 172: 108–112 (1988)) until the trypsin activity was less than 0.5%. Anhydrotrypsin was coupled to cyanogen bromide activated Sepharose 4B according to the manufacturer's instructions (Pharmacia). Chromatography columns were equilibrated with 0.1 M Tris-Cl, pH 8.5, 5 mM $MgCl_2$, 3 mM PMFS. Proteins that were bound to the column were eluted with 0.5 M NaOAc buffer containing 0.5 M NaCl by decreasing the pH from 7.0 to 2.0. Absorbance at 280 nm (nanometers) was used to follow the elution of the bound proteins. Fractions that inhibited bovine trypsin were pooled, dialyzed and lyophilized.

Size-exclusion chromatography (SEC) was performed at room temperature, 18–28° C., on affinity purified trypsin and anhydrotrypsin fractions. A 1.5×100 cm (centimeter) column of Sephadex G-50 was equilibrated with 50 mM NaOAc, 0.25 M NaCl, pH 5.0. Two to five milligrams (mg)

of affinity purified trypsin inhibitor was applied to the column and separated at a flow rate of 15 ml/hr. 2.5-ml fractions were collected. Alternatively, trypsin inhibitor protein was separated by HPLC on a Superose 12 column. Samples were heated at 100° C. for 5 minutes in the presence of 2 mM 2-mercaptoethanol prior to application to the column. The column was equilibrated with degassed 50 mM sodium phosphate buffer, pH 7.0, 0.15 M NaCl. The flow rate was controlled at 0.5 ml/min. 0.5 ml fractions were collected for 20–60 minutes. Fractions which exhibited trypsin activity were pooled and dialyzed against water.

Ion-exchange chromatography was used to separate large (high molecular weight) trypsin inhibitors from other fractions. Large TIs were separated on a 1.5×5 cm anion-exchange column containing BioRad Q5 which had been equilibrated with 40 mM ethanolamine-HCl, pH 9.5. TIs were eluted using a linear gradient from 0 to 0.15 M NaCl. Two-milliliter fractions were collected, tested for inhibition of bovine trypsin and absorbance at 280 nm was measured.

Crude P. macroloba extracts were extensively dialyzed against deionized water at 4EC for several days using a technique combining two molecular weight cutoff (MWCO) membranes or tubings (3,500/10,000 or 3,500/14,000). The higher limit MWCO membrane or tubing contained the crude extract and was placed inside the 3,500 membrane. Deionized water was changed at 12 hour intervals. The separated fractions outside the higher MWCO membrane were collected and subjected to affinity chromatography. When desired, the same tubing combinations can be used to separate affinity purified trypsin inhibitors. Fractions from SEC were also dialyzed against water using different MWCO membranes.

SDS-PAGE was used to separate components and determine their subunit molecular weights and purity. The procedure was carried out according to the method of Laemmli (U. K. Laemmli, Nature 227: 680–685 (1970)) using two types of gel, a 12 to 15% polyacrylamide gel or a 10 to 20% gradient polyacrylamide gel. Protein samples were denatured by boiling for three minutes in SDS buffer (BioRad) with 2 mM 2-mercaptoethanol. Selected samples, referred to herein as native samples, were not boiled prior to electrophoresis. The estimated molecular weights of trypsin inhibitors were estimated by electrophoresis on gradient SDS-PAGE gels of 10–20% polyacrylamide under conditions given by Hammer (B. C. Hammer et al. (1989) Phytochemistry 28: 3019–3026). Proteins were detected by staining with Commassie Brilliant Blue R-250 (CBB R-250). Inhibitory activity was detected using the assay of Ureil and Berges (J. Ureil et al. (1968) Nature 218: 578–580) as modified by Rathburn (G. Pearce et al. (1993) Plant Physiol. 102: 639–644).

Trypsin inhibitory activity was determined. See, for example Yamamoto et al. (1983) J. Biochem. 94: 849–863; Kim et al. (1985) J. Biochem. 98: 435–448; and Richardson et al. (1986) Biochem. Biophys. Acta 872: 134–140. The activity of the inhibitors is expressed in Inhibition Units (IU), where 1 IU is the amount of inhibitor needed to reduce BAPNA ($e=8.8\ \mu mol^{-1} cm^2$) hydrolysis by 1 $\mu$mol/min at 25° C.

Figure 1:
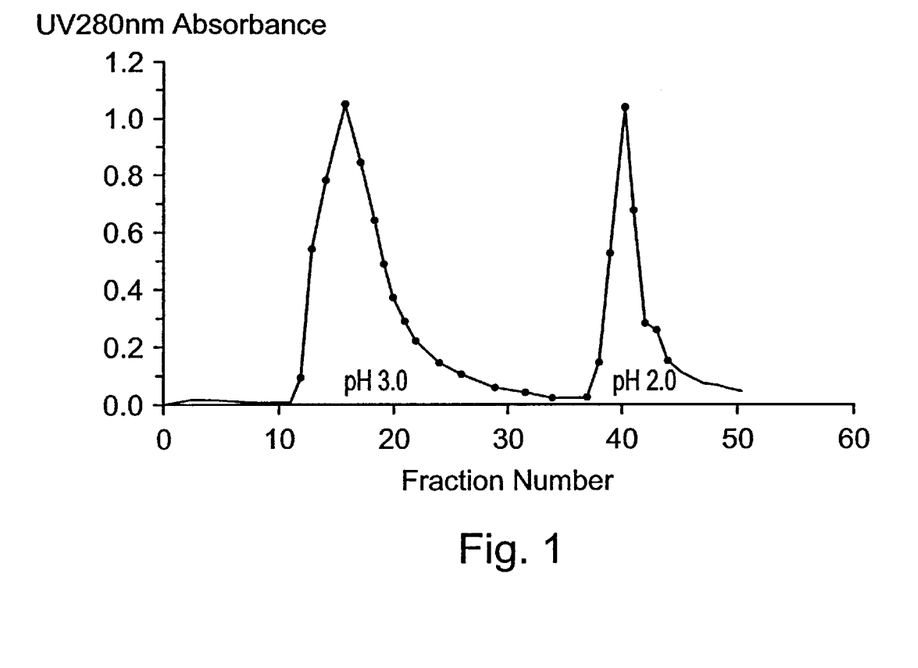
FIG. 1 illustrates an affinity chromatogram of the isolated trypsin inhibitors obtained from P. macroloba in accordance with the invention.

FIG. 1 illustrates the use of affinity chromatography to isolate trypsin inhibitor(s) from P. macroloba. A crude extract was applied directly to a 1×20 cm column and the column was washed until the absorbance of the eluate was of the less than 0.02 at 280 nm. The column was then eluted using 0.5 M NaOAc, 0.5 M NaCl buffer from pH 2.0 to 7.0 and fractions were collected.

Figure 2A:
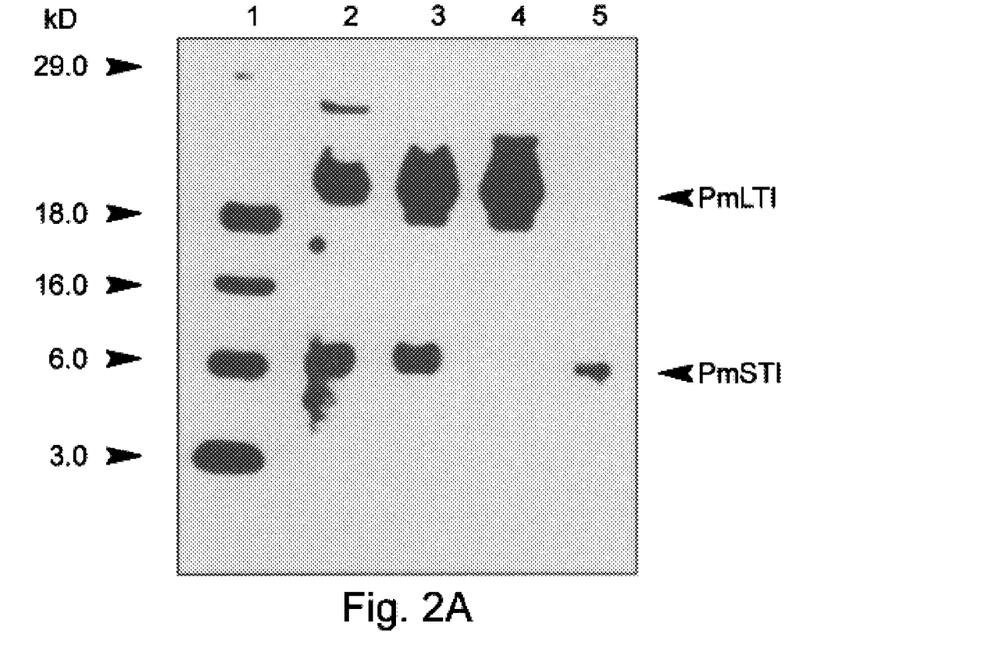
FIG. 2A illustrates the SDS-PAGE separation of P. macroloba trypsin inhibitors in accordance with the invention.
Figure 2B:
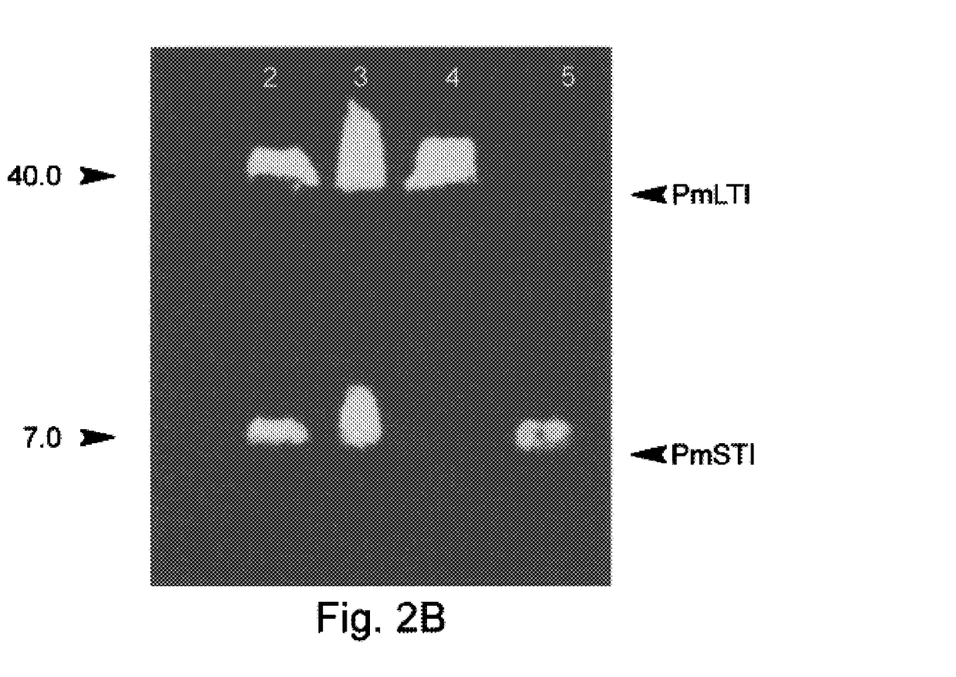
FIG. 2B illustrates in-gel trypsin inhibitory activity staining.

FIGS. 2A and 2B illustrate SDS-PAGE of P. macroloba inhibitors. In FIG. 2A, a silver stain was used. The sample was mixed with non-reducing buffer (BioRad) and heated for 3 minutes at 100° C. prior to electrophoresis.

FIG. 2B illustrates in-gel inhibitory activity staining. A sample was mixed with non-reducing sample buffer and was not heated. The lanes represent the following: Lane 1, molecular weight markers; Lane 2, crude Pm extract; Lane 3, Affinity-purified PmTI; Lane 4, PmLTI; and Lane 5, PmSTI.

FIG. 1 illustrates the two major peaks that were isolated from trypsin affinity chromatography (TAC) using pH 3.0 and 2.0 buffers. The pH 2.0 fraction was identified as denatured protein and did not inhibit trypsin activity. The pH 3.0 fraction contains two classes of trypsin inhibitors designated herein as P. macroloba large trypsin inhibitor (PmLTI) and P. macroloba small trypsin inhibitor (PmSTI) as shown in FIGS. 2A and 2B. In addition, several additional polypeptides were obtained. Tests were conducted to determine whether PmLTI was cleaved by trypsin during purification and whether PmSTI was a portion of the degraded PmLTI. Crude extracts were subjected to electrophoresis, and inhibition activity was determined using an in-gel trypsin inhibition assay. Two trypsin inhibitors of the same mobility as that of the affinity purified pH 3.0 fraction were detected as shown in FIG. 2. These results indicate that at least two different trypsin inhibitors, PmLTI and PmSTI, exist in P. macroloba seeds.

Anhydrotrypsin affinity chromatography (ATAC) was used to determine whether PmSTI and the additional polypeptides seen in TAC were the result of cleavage of PmLTI by fully active trypsin during affinity chromatography. In this purification, the active site of trypsin was blocked. Trypsin inhibitor isolated by ATAC was considered to be without modification. Five bands were observed on the SDS-PAGE of PmTI isolated by this procedure and reduced. In contrast, heat denatured Pm TI showed only one band of Mr=21.5 kDa (data not shown). By comparison to the PmTI isolated from the fully active trypsin affinity column, it was concluded that Pm TI was degraded by trypsin during affinity chromatography purification.

PmSTI/PmLTI ratio was found to be very low. In the affinity purified products, PmSTI could not be detected in stained SDS-PAGE gel despite the fact that in-gel inhibition assay gave a large clear spot for this inhibitor.

Figure 3:
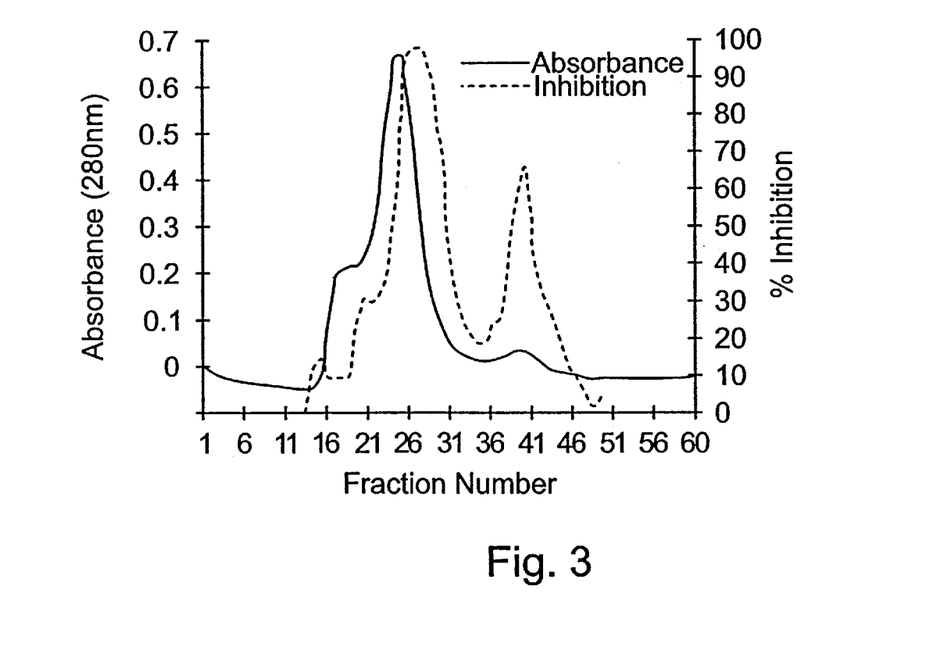
FIG. 3 illustrates the separation by Sephadex G-50 of two types of trypsin inhibitors obtained in accordance with the invention.

FIG. 3, gel filtration on Sephadex G-50 carried out at pH 5.0, shows two well-separated peaks corresponding to PmLTI and PmSTI. SDS-PAGE results indicate that peak I is purified PmLTI and peak II is PmSTI, admixed with a small amount of inactive PmLTI, whose activity was detected by the in-gel assay of FIG. 2.

Figure 4:
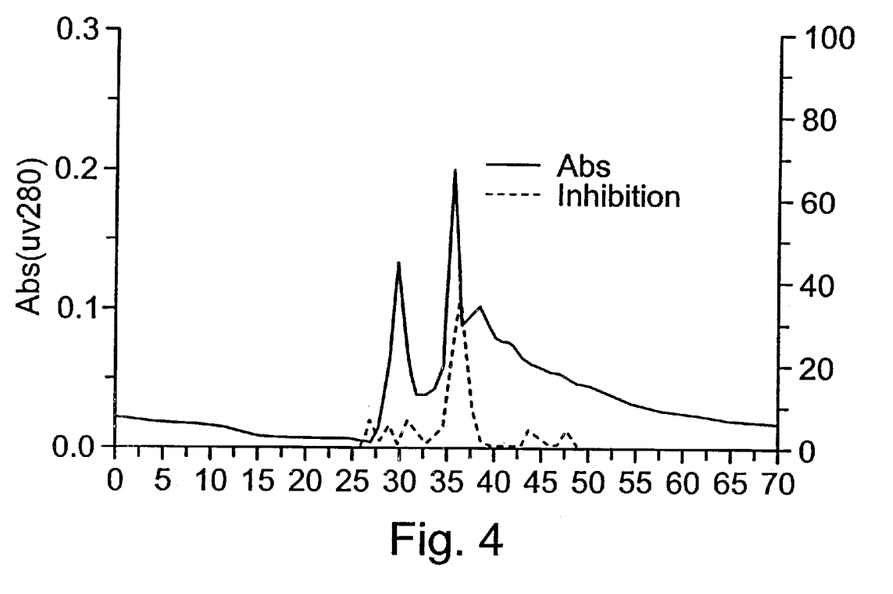
FIG. 4 illustrates the separation by HPLC of a trypsin inhibitor mixture obtained according to the invention and heat treated for 3 minutes by boiling in aqueous solution.

FIG. 4 illustrates the separation of heat-treated PmTI by HPLC. An aqueous sample was boiled for 3 minutes, applied to a Superose column, and eluted.

Figure 5:
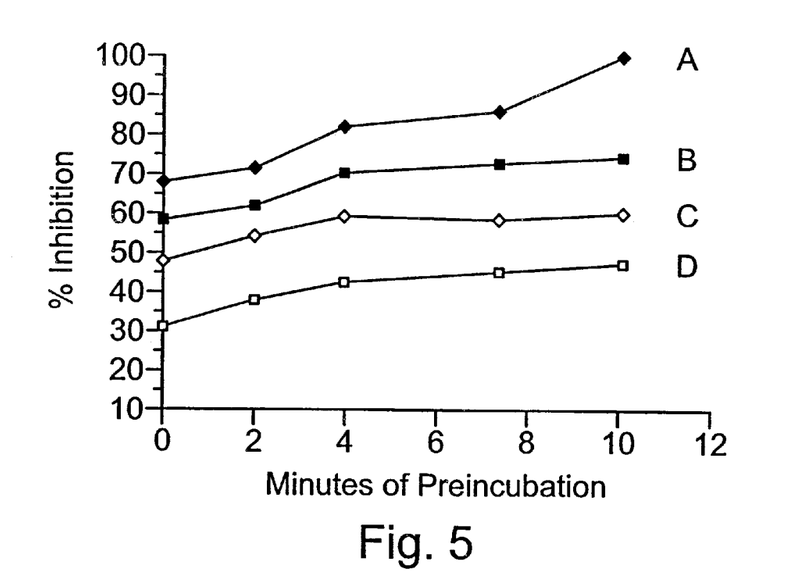
FIG. 5 illustrates an inhibition assay of trypsin and P. macroloba trypsin inhibitors in BAPNA substrate incubated over time.

FIG. 5 is an inhibition assay, over incubation time, of samples containing trypsin and PmTI. Samples were prepared using a solution of 0.1 M Tris-Cl, pH 9.5. The samples (A, B, C and D) contained 5 $\mu$g trypsin and PmTI in amounts of: (A) 7.2 nanograms, (B) 14.4 nanograms, (C)10.8 nanograms and (D) 7.2 nanograms. BAPNA substrate in the amount of 2.5 mM was added to each sample. Trypsin activity was measured at various time points after the addition of the BAPNA substrate.

In order to fully understand the chromatographic behavior of both PmLTI and PmSTI, reduced and native affinity purified trypsin inhibitors were separated over a size-exclusion chromatography (SEC) column. Protein profiles with and without reduction with p-mercaptoethanol were similar, indicating disulfide bridges are not essential to maintain the dimeric structures. The heat stability of PmSTI, discussed below, can be used to distinguish PmSTI from PmLTI and other trypsin inhibitors. A sample of PmSTI was heat treated, chromatographed on a SEC column and showed three product peaks. Only peak II was active, indicating that this peak corresponds to PmSTI. Peak III was close in molecular weight to Peak II, but did not exhibit any inhibition activity.

PmSTI is a small polypeptide with a subunit in the 6–9 kDa range, generally about 7 kDa molecular weight, and is present in low concentrations in *P. macroloba* seeds. Large quantities of PmSTI can be obtained by first dialyzing crude extracts using a double dialysis method. PmSTI, along with other low molecular weight proteins, dialyzed out of the 12–14 kDa membrane and was collected within a 3.500 MWCO membrane. The PmSTI fraction was further purified by affinity chromatography followed by gel filtration.

The subunit molecular weight of the trypsin inhibitors was determined by 10–20% SDS-PAGE. The two iso-inhibitors (isoforms) constituting PmLTI were found to have molecular weights of approximately 43 and 39 kDa. Denaturing the PmLTI fraction by heating converted it into a species having a molecular weight of about 21.5 kDa. In-gel trypsin inhibition assay of PmLTI separated on an IEF gel indicates that it is composed of two active proteins of pI 8.8 and 8.5. Similar testing of PmSTI indicates it is a low molecular weight polypeptide having a molecular weight of about 7 kDa and contains two active proteins of pI 8.2 and 5.0. [Data not shown]. These results indicate both PmLTI and PmSTI contain two iso-inhibitors of nearly the same molecular weight.

Heating affinity purified *P. macroloba* TI's has a profound effect on their inhibition activity. A crude extract, containing both PmLTI and PmSTI, had an inhibition activity of 2.2 IU/mg TI before heating and 3.7 IU/mg TI after heating at 70° C. for 5 minutes. PmLTI completely loses activity after heating at 100° C. for 5 seconds. In contrast, PmSTI retained activity after boiling at 100° C. for 30 minutes. PmSTI did lose activity after boiling for 5 minutes under reducing conditions.

Amino Acid Sequence Information

The N-terminal sequence of PmLTI has been determined and is shown, in SEQ ID NO: 3. The Edman degradation method was used for amino acid sequencing. The sequencing was performed on an Applied Biosystems 477A Protein Sequencer having a 120A Analyzer.

Internal Sequences

Internal amino acid sequence data was determined after cleavage of the protein with cyanogen bromide and separation of the fragments by SDS PAGE. peptides were blotted to PVDF and subjected to automated sequence analysis.

Enzymatic Assay of the Inhibitory Activity of Pm TIs

The inhibitory activity of *P. macroloba* TIs was determined by enzymatic assay using the method and materials described by J. Chun et al. (1994) *J. Econo. Ento.* 87: 1754–1760, which include the procedures of: C. J. Lenz et al. (1979) *J. Insect Physiol.* 25: 487494; Y. Takesue et al. (1989) *J. Biochem.* 105: 998–1001; S. E. McEwen et al. (1980) *Insect Biochem.* 10: 563–567; J. F. Myrtle and W. J. Zell (1980) *Clin. Chem.* 21: 1469–1473; and K. K. Thomas and J. L. Nation (1984) *Comp. Biochem. Physiol. A Comp. Physiol.* 79:297–304. For these enzyme inhibition studies, purified TI's were incubated with appropriate amounts of buffer and bovine trypsin or *Helicoverpa zea* (*H. zea*) midgut trypsin at 27° C. The substrates were then added and the reactions were performed as described in the referenced method(s).

The results of inhibitory activity assays of the *P. macroloba* TI's against bovine and *H. zea* trypsins are given in Table 1. The specific activity values were 2.78 IU/mg TI for bovine trypsin and 3.93 IU/mg TI for *H. zea* midgut trypsin. The specific activity of PmSTI was 50.94 IU/mg TI for bovine trypsin and 14.23 IU/mg TI for *H. zea*. PmTIs obtained from the fully active trypsin affinity column (TAC) show lower trypsin inhibition activity than PmTIs obtained from the anhydrotrypsin affinity column (ATAC). This suggests that PmTI is modified by trypsin in such a manner as to reduce the inhibitory effectiveness of the PmTI. It was also found that PmTI was completely bound to trypsin in about 10 minutes.

TABLE 1

Inhibitory Activity of PmTIs and Soybean TI

| Sample | Protein (mg) | Bovine Tr.[1] | | H. zea Midgut Tr.[1] | |
|---|---|---|---|---|---|
| | | IA[2] | SA[3] | IA[2] | SA[3] |
| A[4] | 3.1 | 0.119 | 0.038 | 0.245 | 0.079 |
| B[5] | 2.0 | 4.959 | 2.48 | 7.457 | 3.729 |
| C[6] | 2.0 | 5.567 | 2.784 | 7.855 | 3.928 |
| D[7] | 0.6 | 30.566 | 50.940 | 8.538 | 14.230 |
| E[8] | N/A | N/A | 1.016 | N/A | 0.845 |
| F[9] | N/A | N/A | 5.030 | N/A | 2.101 |

Notes:
[1]Tr = trypsin.
[2]IA = Inhibitory Activity in IUs.
[3]SA = Specific Activity in IU/mg protein.
[4]A = Crude Extract.
[5]B = Affinity purified TI.
[6]C = PmLTIs.
[7]D = PmSTIs.
[8]E = Kunitz TI.
[9]F = Bowman-Birk TI.

Biological Assays with PmTIs

Neonate insect pests were reared on artificial diets containing PmTIs, either crude or purified as taught herein, which were either topically applied to the diet surface or incorporated into the diet as taught by Czapla and Lang (T. H. Czapla and B. A. Lang, *J. Econo. Ento.* 83 (6): 2480–2485 (1990)). The culture tray used in the bioassays was divided into treatment groups. One or a plurality of PmTIs were screened in each tray, each PmTI being applied to a plurality of cells. Each cell was infested with one neonate larvae. A Mylar film with ventilation holes was affixed to the top of each tray to prevent escape.

For the topical assays, the TI was prepared in 0.1 M phosphate buffered saline (PBS) buffer (pH 7.8) as a 2% solution. Seventy-five microliters of solution were pipetted onto Stoneville medium in each cell. The culture tray was rotated to ensure equal distribution of the inhibitor. The cells were infected and sealed as described above. The control was 75 µl of 0.1 M PBS per cell.

For the diet incorporation assays, Stoneville medium was prepared in standard fashion but with only 90% of the prescribed water. PmTI was added such that the amount in the diet was in the range of 1–5 µg/g. The control treatment consisted of 0.9 ml PBS buffer added to 8.1 g of medium. The medium was poured into the cells and the cells were then infested and covered as described above. Insect weights were determined at Day 7 and are given in Tables 2–4. The data in Tables 2 and 3 were obtained using extracts from *P. macroloba* which contain both the PmLTI and the PmSTI component. The data in Table 4 was obtained using PmTI that was separated into its PmLTI and PmSTI components.

The data in Table 4 were obtained using corn rootworm (CRW) neonate larvae. While the data in Table 4 indicates that PmLTI is effective against CRW and PmSTI is not effective against CRW, the data in Table 8 indicates that PmSTI is effective against other insect pests.

TABLE 2

European Corn Borer Bioassay with PmTIs

| μg TI/cup | Avg. Wt. | % Wt. Change | % Mortality |
|---|---|---|---|
| A. Topical application-Weights at Day 7 | | | |
| 0 | 4.93 mg | — | 6.25 |
| 10 | 4.55 mg | −7.7 | 6.25 |
| 25 | 3.99 mg | −19.1 | 6.25 |
| 50 | 3.86 mg | −21.7 | 6.25 |
| B. Incorporated into diet-Weights at Day 7 | | | |
| Assay 1 | | | |
| 0 | 5.07 mg | — | 6.25 |
| 50 | 6.45 mg | +27.2 | 18.75 |
| 100 | 3.35 mg | −33.9 | 6.25 |
| 250 | 4.18 mg | −17.6 | 25.00 |
| Assay 2 | | | |
| 0 | 4.88 mg | — | 25.00 |
| 100 | 3.41 mg | −30.1 | 18.75 |
| 250 | 2.97 mg | −39.1 | 6.25 |
| 500 | 2.71 mg | −44.5 | 43.75 |

TABLE 3

H. zea Bioassay with PmTIs
Incorporated into Diet-Weight at Day 7

| μg/ml | Avg. Wt. | % Wt. Change |
|---|---|---|
| Assay 1 | | |
| 0 | 92 mg | — |
| 1.5 | 101 mg | +9.9 |
| 3.0 | 101 mg | +9.8 |
| 6.0 | 54 mg | −41.3* |
| Assay 2 | | |
| 0 | 56 mg | — |
| 3 | 55 mg | −1.8 |
| 6 | 56 mg | 0 |
| 9 | 36 mg | −35.7 |
| Assay 3 | | |
| 0 | 182 mg | — |
| 10 | 198 mg | +8.8 |
| 45 | 243 mg | +33.5 |

Note:
*Comparison significant at the 0.05 level with Sheffe=s test.

TABLE 4

Corn Rootworm Bioassay with PmLTI and PmSTI*

| PmTI, mg/ml | Weight | % Loss v. Control | % Mortality |
|---|---|---|---|
| Control, O | 2.8 | — | 7 |
| LTI, 0.2 | 2.8 | 0 | 29 |
| LTI, 0.3 | 2.8 | 0 | 29 |
| LTI, 0.8 | 0.7 | 83 | 57 |
| Control, 0 | 3.2 | — | 0 |
| STI, 0.6 | 3.2 | 0 | 0 |

Note:
*Assay conducted with corn rootworm (CRW) neonate larvae. The PmLTI and PmSTI were incorporated into the diet as described above.

Trypsin Inhibitor Comparisons

Tables 5, 6 and 7 compare PmTI to Bowman-Birk and Kunitz trypsin inhibitors. The results for bovine chymotrypsin in Table 5 indicate that the activity of PmTI falls between that of Bowman-Birk and Kunitz, the Bowman-Birk being the least active. The results for the inhibition of H. zea midgut trypsin in Table 6 indicate that the activity of PmTI at pH 8.0 lies between that of the Bowman-Birk and Kunitz inhibitors, and at pH 9.5 and 10.0 PmTI has a higher level of activity. The results for the inhibition of bovine trypsin in Table 7 indicate that the activity of PmTI falls between that of the Bowman-Birk and Kunitz Tis.

TABLE 5

Micrograms of Trypsin Inhibitors to Inhibit
1.6 μg Bovine Chymotrypsin by 50%

| | P. macroloba TI | Bowman-Birk TI | Kunitz TI |
|---|---|---|---|
| pH 8.0* | 8.6 | 1.3 | 11.8 |
| pH 9.0* | 4.4 | 1.0 | 8.4 |
| pH 9.5* | 2.1 | 1.0 | 23.6 |

Note:
*All solutions are 0.1M Tris-Cl.

TABLE 6

Nanograms of Trypsin Inhibitors to Inhibit
H. zea Midgut Trypsin by 50%

| | P. macroloba TI | Bowman-Birk TI | Kunitz TI |
|---|---|---|---|
| pH 8.0* | 660 | 744 | 323 |
| pH 9.5* | 939 | 974 | 1467 |
| pH 10.0* | 925 | 1196 | 1401 |

Note:
*All solutions are 0.1M Tris-Cl.

TABLE 7

Nanograms of Trypsin Inhibitors to Inhibit
5 μg Bovine Trypsin by 50%

| | P. macroloba TI | Bowman-Birk TI | Kunitz TI |
|---|---|---|---|
| pH 8.0* | 835 | 754 | 1551 |
| pH 9.5* | 765 | 637 | 1071 |
| pH 10.0* | 787 | 754 | 1264 |

Note:
*All solutions are 0.1M Tris-Cl

Table 8 B presents bioassay data for the Pm small trypsin inhibitor (PmSTI) against both European corn borer (Ostrina nubilalis) and the bacterial feeding nematode Caenorhabditis elegans (C. elegans). C. elegans is used by those in the art as a model system to identify feeding factors to control plant parasitic nematodes such as root knot, cyst and lesion nematodes.

The data in Table 8 A shows that the PmSTI gene expressed in E. coli as a fusion protein reduces the growth and survival of Ostrina nubilalis which have been reared on diets containing heat-killed E. coli cells expressing the protein. All cells were induced with IPTG. The soluble PmSTI content of the cells was very low. The methods for growing the E. coli cells are well known to those skilled in the art. Typically, the weight of larvae fed E. coli cells containing the PmSTI gene was less than half the weight of larvae fed cells which did not contain the PmSTI gene.

As a result of the low concentration of soluble PmSTI in the E. coli cells, the differences in weight between larvae fed cells containing PmSTI and the control larvae are of more significance than the mortality rate. The data clearly indicates that ingestion of PmSTI, even at low concentrations, has a significant effect on larval growth. The inability of larvae to gain weight and mature will ultimately affect their survival and ability to reproduce. This observation is in accordance with the data presented in Tables 2 and 4.

TABLE 8

PmSTI Bioassay Data

A. European corn borer

|  | % Mortality | Larval Wt.[1] |
|---|---|---|
| Control,[2] no PmSTI gene | 25 | 7.6 |
| Buffer control, no gene | 13.3 | 7.9 |
| PmSTI gene[3] | 18.7 | 3.5 |
| PmSTI plus kanamycin | 18.7 | 3.5 |

B. *C. elegans*

|  | % Mortality[4] |
|---|---|
| Control | — |
| PmSTI gene | 98.8 |

Notes:
[1] Larval weight at the end of the 7 day test.
[2] Heat-killed *E. coli* cells without PmSTI gene.
[3] Heat-killed *E. coli* cells expressing PmSTI gene.
[4] Mortality at end of 10 day test.

The PmSTI protein was cloned and the amino acid sequence was deduced from the sequence of the cDNA clone as shown in SEQ ID NO: 2.

All publications and patent applications mentioned in the specification are indicative of the level of those skilled in the art to which this invention pertains. All publications and applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A stably transformed plant comprising in its genome a chimeric gene, said chimeric gene comprising a nucleotide sequence encoding a protein having insecticidal activity wherein said protein is about 6–9 kDa in size and exhibits trypsin inhibiting activity, wherein said nucleotide sequence hybridizes to the nucleotide sequence of SEQ ID NO:1, or a complement thereof, under stringent conditions defined by a wash stringency of 0.3 M NaCl, 0.03 M sodium citrate, 0.1% SDS at 70° C.

2. Seed of the transformed plant of claim 1, wherein said seed comprises in its genome the chimeric gene of claim 1.

3. The transformed plant of claim 1 wherein said transformed plant is a dicot.

4. The transformed plant of claim 1 wherein said transformed plant is a monocot.

5. The transformed plant of claim 4 wherein said monocot is maize.

6. Seed of the transformed plant of claim 4, wherein said seed comprises in its genome the chimeric gene of claim 1.

* * * * *

UNITED STATES PATENT AND TRADEMARK OFFICE
CERTIFICATE OF CORRECTION

PATENT NO.   : 6,384,302 B1                                                    Page 1 of 1
DATED        : May 7, 2002
INVENTOR(S)  : Chen et al.

It is certified that error appears in the above-identified patent and that said Letters Patent is hereby corrected as shown below:

Title page,
Item [54], the title was amended to read -- PLANTS TRANSFORMED WITH NUCLEIC ACIDS ENCODING TRYPSIN INHIBITORS HAVING INSECTICIDAL PROPERTIES --.
Item [73], Assignee, add -- Board of Regents for the University of Oklahoma, Norman, OK (US) --.
Item [56], References Cited, U.S. PATENT DOCUMENTS, "5,672,680 A", "Chen et al." should read -- Rathburn et al. --.

Signed and Sealed this

First Day of July, 2003

JAMES E. ROGAN
*Director of the United States Patent and Trademark Office*